United States Patent [19]

Ruzicka et al.

[11] Patent Number: 4,742,716

[45] Date of Patent: May 10, 1988

[54] SAMPLE INTRODUCTION SYSTEM FOR NONSEGMENTED CONTINUOUS FLOW ANALYSIS

[75] Inventors: Jaromir Ruzicka, Holte; Elo Hansen, Lyngby, both of Denmark

[73] Assignee: Bifok AB, Sollentuna, Sweden

[21] Appl. No.: 6,262

[22] Filed: Jan. 20, 1987

Related U.S. Application Data

[63] Continuation of Ser. No. 796,093, Nov. 7, 1985, abandoned.

[51] Int. Cl.⁴ ............................................. G01N 1/00
[52] U.S. Cl. ................................................. 73/864.81
[58] Field of Search ........... 73/864.81, 864.85, 863.23, 73/863.83, 863.84, 864, 864.21, 864.22, 864.34, 864.73, 61.1 C; 436/52, 50, 53, 54; 422/81, 82

[56] References Cited

U.S. PATENT DOCUMENTS

| 3,365,951 | 1/1968 | Jentzsch et al. | 73/864.81 |
|---|---|---|---|
| 3,511,080 | 5/1970 | Roof | 73/864.81 |
| 3,676,649 | 7/1972 | Burk | 73/61.1 C |
| 3,698,870 | 10/1972 | Jong | 422/82 |
| 3,699,004 | 10/1972 | Skeggs | 422/82 |
| 3,795,149 | 3/1974 | Gillette et al. | 73/864.22 |
| 3,800,593 | 4/1974 | Bradley | 73/864.81 |
| 4,022,575 | 5/1977 | Hansen et al. | 436/52 |
| 4,165,644 | 8/1979 | Brandt et al. | 73/864.83 |
| 4,199,988 | 4/1980 | Riegger | 73/864.85 |
| 4,441,374 | 4/1984 | Suzuki | 73/864.81 |
| 4,464,940 | 8/1984 | Pospisil | 73/864.21 |
| 4,520,108 | 5/1985 | Yoshida et al. | 73/864.81 |

*Primary Examiner*—Stewart J. Levy
*Assistant Examiner*—Robert R. Raevis
*Attorney, Agent, or Firm*—Poms, Smith, Lande & Rose

[57] ABSTRACT

Sample injection system for nonsegmented, continuous flow analysis comprising an inlet channel, an analyzer channel and a carrier stream channel connected in a confluence point, an aspirating pump in the analyzer channel, a carrier stream pump in the carrier stream channel with a higher capacity than the aspirating pump and an analyzer. In a first step prior to the sample injection, the carrier stream pump forwards carrier stream to the confluence point, the aspirating pump sucks carrier stream from the confluence point, at a lower rate than the carrier stream pump and an outflow of carrier stream drains through the inlet channel. In a second step, the carrier pump is stopped, the inlet end of the inlet channel is brought in contact with the sample solution, and the aspirating pump sucks sample into the inlet channel and the analyzer channel. In the third step, the carrier pump is restarted, whereby the sample in the analyzer channel is aspirated into the analyzer, and all the sample in the inlet channel is pressed out into the waste. The analyzer may be a flow through detector, dialyzer, or any other apparatus for analysis. The performance can also be made as a multichannel system for simultaneous analysis of several components in different analyzers.

9 Claims, 1 Drawing Sheet

SAMPLE INTRODUCTION SYSTEM FOR NONSEGMENTED CONTINUOUS FLOW ANALYSIS

This is a continuation of co-pending application Ser. No. 796,093 filed on Nov. 7, 1985, and now abandoned.

BACKGROUND OF THE INVENTION

The successful operation of any flow injection analysis (FIA) system requires injection of a well-defined sample zone into the analyzer channel, where the zone disperses in a controlled manner on its way towards and through the detector to be measured upon (cf. U.S. Pat. Nos. 4,022,575; 4,177,677; 4,224,033; 4,314,824; 4,227,973; and 4,315,754, and U.S. patent applications Ser. Nos. 48,002; 296,256; 320,483; and 385,049). The injection devices designed for this purpose so far can be divided into two categories: (a) volume based injection; and (b) time based injection, or a combination thereof. In category (a) the injection is based on the physical entrapment of sample solution into a geometrically well-defined volumetric cavity and subsequent transfer (injection) of the thus formed sample zone into a nonsegmented carrier stream (cf. the above mentioned FIA monograph and U.S. Pat. Nos. 4,177,677 and 4,224,033). Category (b) is based on aspiration of sample solution at a constant flow rate for a fixed period of time into a well-defined section of a flow through channel, from where the metered sample zone is injected into a nonsegmented carrier stream by a combination of hydrostatic and hydrodynamic forces—the socalled hydrodynamic injection procedure (cf. U.S. patent application Ser. No. 385,049).

SUMMARY OF THE INVENTION

The present invention involves a sample injection system for nonsegmented continuous flow analysis (FIA) including an inlet channel, an analyzer channel and a carrier stream channel which are connected in a confluence point. The system further includes an aspirating pump in the analyzer channel and a carrier stream pump in the carrier channel with a higher capacity than the aspirating pump. An analyzer or detector is included in the analyzer channel.

In a first step prior to the sample injection, the carrier stream pump forwards carrier stream to the confluence point, the aspirating pump sucks carrier stream from the confluence point at a lower rate than the carrier stream pump, and an outflow of carrier stream drains through the inlet channel.

In a second step, the carrier pump is stopped, the inlet end of the inlet channel is brought in contact with the sample solution, and the aspirating pump sucks sample into the inlet channel and the analyzer channel.

In the third step, the carrier pump is restarted, whereby the sample in the analyzer channel is aspirated into the analyzer, and all the sample in the inlet channel is pressed out into the waste.

The analyzer may be a flow through detector, dialyzer, or any other apparatus for analysis. The performance can also be made as a multichannel system for simultaneous analysis of several components in different analyzers.

DETAILED DESCRIPTION OF THE INVENTION

The purpose of the present invention is to describe a simplified and improved development of the hydrodynamic injection approach, which is based on the use of a confluence point at which a well-defined sample zone is formed by means of the alternate motion of sample and carrier streams. The principle is best explained by reference to FIGS. 1A, 1B and 1C.

Figure 1A:
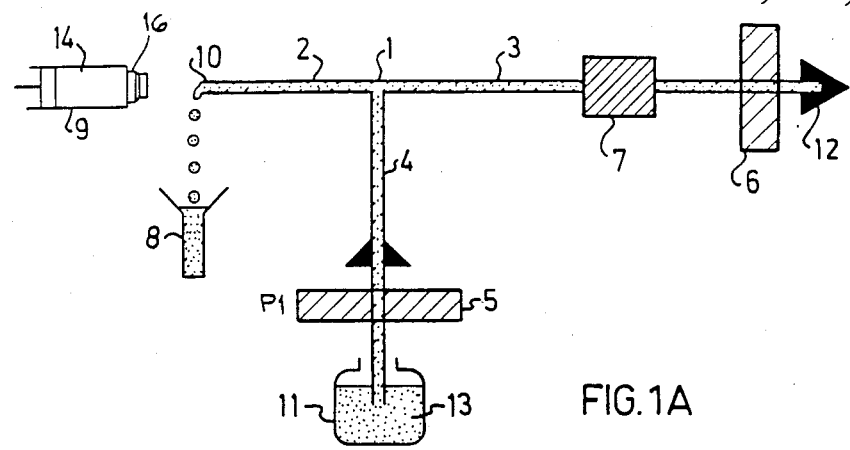
FIG. 1A is a schematic side view of the preferred exemplary embodiment prior to injection of the sample solution.
Figure 1B:
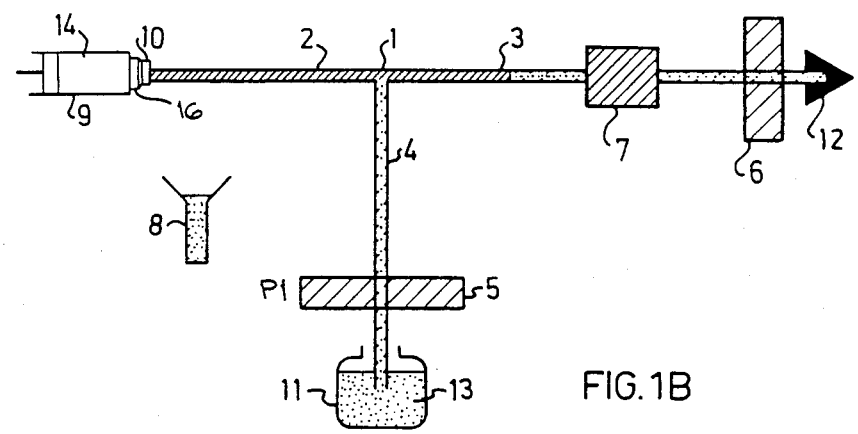
FIG. 1B is a schematic side view of the preferred exemplary embodiment during sample aspiration.
Figure 1C:
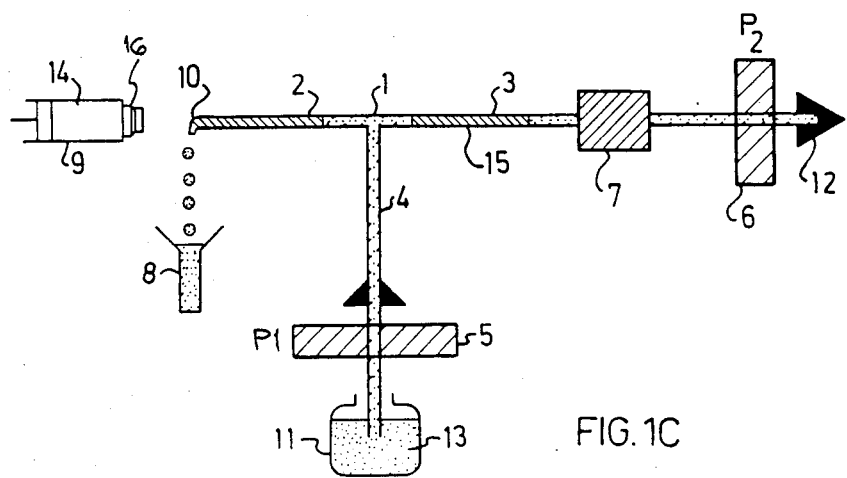
FIG. 1C is a schematic side view of the preferred exemplary embodiment during same injection.

FIG. 1A is a schematic representation of step 1 of the present invention showing the system prior to injection of the sample solution. FIG. 1B is a schematic representation of step 2 of the present invention showing the system during sample solution aspiration. FIG. 1C is a schematic representation of step 3 of the present invention showing the system during sample solution injection. In the figures, 1 is the confluence point; 2 is the inlet channel; 3 is the analyzer channel; 4 is the carrier stream channel; 5 is the carrier stream pumping device; 6 is the analyzer channel pumping device; 7 is the analyzer situated in the analyzer channel; 8 is the waste receptacle; 9 is the sample source; 10 is the inlet end of the inlet channel; 11 is the reservoir of the carrier stream fluid; 12 is the waste outlet for the analyzer channel; 13 is the carrier solution; 14 is the sample solution; and 15 is the injected sample zone. The operational cycle of the system comprises three sequential steps, each of which is represented in FIGS. 1A-C, details being as follows.

STEP 1 (FIG. 1A), i.e. prior to injection of sample solution: Pump P1 (5) pumps carrier stream solution 13 towards the confluence point 1 at a higher volumetric pumping rate than pump P2 (6) which by its mode of action aspirates the liquid of the analyser channel 3, that is, pumps away from the confluence point, resulting in a positive outflow of carrier stream solution through the inlet channel 2 and via 10 into waste 8, while sections 3 and 7 concurrently are filled with carrier stream solution flowing towards waste 12.

STEP 2 (FIG. 1B), i.e., sample aspiration: Pump P1 (5) is stopped and the column of carrier stream solution 13 in the carrier stream channel 4 is held still, while pump P2 is maintained operating thereby aspirating sample solution 14 from container 9 which now has been moved into contact with inlet end 10.

STEP 3 (FIG. 1C), i.e., sample injection: While pumping by P2 is maintained, pumping by pump P1 is resumed and sample source 9 is withdrawn. Thus all sample solution 14 to the left of the confluence point 1 is forced in countercurrent fashion from the sample inlet into waste 8, while all sample solution in the form of an injected sample zone 15 to the right of the confluence point 1 is aspirated, followed by carrier stream solution 13, through the analyzer channel 3 and into the analyzer 7 for further treatment and measurement. As both pumps P1 and P2 continue pumping, all sample material is eventually expelled from the system either via the inlet channel 10 or via the analyser channel 7, the pump P2 (6) and the waste outlet 12, and the system is thus reestablished for the next sampling period, being now, in fact, in STEP 1 again.

While the explanation given above describes the principles of the new, proposed mode of injection, it should be noted that variations on this theme are possible without constraining the spirit of the invention. Thus, if a sample is too concentrated to be processed by the analyser 7, an additional dilution may be executed at the confluence point 1 by decreasing—during the duration of STEP 2—the pumping rate of the inflowing carrier stream below the apiration rate of pump P2 (6), instead of stopping P1 entirely. Furthermore, if the carrier stream would contain a reagent with which the sample solution should be mixed for the purpose of an intended chemical reaction, which is to be subsequently monitored in the analyzer 7, an effective mixing can thus be obtained during the passage of material through channel 3 to the analyzer 7. The analyzer 7 may be a flow through detector, or may even comprise a system of channels, detectors, dialyzer, or gas diffusion and pumping units—the only restriction being that the net inflow rate fulfils the conditions stipulated above, i.e., the flow rate through the analyzer 7 is governed solely by the aspiration flow rate of 6.

It is of interest to mention that the countercurrent movement of liquid through channel 2 may be used with advantage if the sampled liquid contains particulate matter which has to be removed prior to automated assay. By placing a filtering device 16 at position 10 particles may be retained on the filter 16 during aspiration of the sample and descarded during the subsequent discharge period (STEP 3).

It is important to emphasize that the repetitive movements of sample solution 14 and the inlet end 10 must be executed in harmony with the countercurrent movement of liquid through channel 2 in such a way that under no circumstances air will enter the analyzer channel 3.

For operation of the injection system in that case where pump P1 is stopped during the sampling period (STEP 2), the injected sample volume $S_v$ can be calculated from the stopped time interval T of pump P1 and the aspiration rate Q of pump P2 and by correcting for the expelled sample liquid contained within the inlet channel 2 of volume $i_v$, i.e.:

$$S_v = (T \cdot Q) - 1_v.$$

The advantages of the new injection system may be summarized as follows:

(1) No moving parts in contact with the handled liquids.

(2) Lesser mechanical complexity than in any valving system.

(3) Ideally suited for microminiaturization.

(4) Ideally suited for integration into microconduits, which without any mechanical moving parts are easy to make, are inexpensive and disposable.

(5) The sample volume—and the sample dispersion—is adjusted by timing sequences rather than by adjusting the volume of a cavity in a valve, that is, electronic computer control rather than mechanical control of the dispersion is exerted.

(6) Less complex than "classical" hydrodynamic injection—only two pumping tubes are required, and the streams do not have to be balanced.

(7) Countercurrent operation of the inlet part of the system, allowing clean-up and/or filtration.

What we claim is:

1. A sample injection apparatus adapted to introduce a well-defined liquid sample segment into a liquid carrier stream of a non-gas segmented continuous flow analysis system, said sample injection apparatus comprising:

an inlet channel having an inlet end and an outlet end; sample means which is selectively connectable to said inlet channel inlet for introducing liquid sample into said inlet channel;

a carrier stream channel having an inlet end and an outlet end;

an analyzer channel having an inlet end which is connected to the outlet ends of said inlet channel and carrier stream channel to provide a confluence point through which liquids may flow between the inlet channel, carrier stream channel and analyzer channel;

first pumping means which is operable at various pumping speeds for pumping a non-gas segmented liquid carrier stream though said carrier stream channel at various selected volumetric flow rates, said flow rates ranging from zero to various predetermined carrier stream flow rates;

second pumping means for pumping non-gas segmented liquid through said analyzer channel at a constant predetermined analyzer stream volumetric flow rate wherein said first pumping means is operable at a first selected pumping speed to provide a carrier stream flow rate that is higher than the analyzer stream flow rate in order to flow carrier liquid from said confluence point through said inlet channel towards said inlet channel inlet end and wherein said first pumping means is operable at a second selected pumping speed to provide a carrier stream flow rate that is lower than the analyzer stream flow rate in order to aspirate non-gas segmented liquid sample into said inlet channel when said sample means is connected to the inlet end of said inlet channel, wherein alternating operation of the first pumping means between said first and second pumping speeds provides aspiration of well-defined liquid sample segments into the liquid carrier stream in said analyzer channel.

2. A sample injection apparatus according to claim 1 which includes more than one analyzer channel.

3. A sample injection apparatus according to claim 1 wherein said analyzer channel includes an outlet end, and said apparatus further includes analyzer means associated with said analyzer channel outlet end for treatment of said non-gas segmented liquid carrier stream and liquid sample segments flowing through said analyzer channel.

4. A sample injection apparatus according to claim 3 wherein said analyzer means includes means for measuring a measurable characteristic of said non-gas segmented carrier stream and liquid sample segment.

5. A sample injection apparatus according to claim 1 wherein filter means are provided in said inlet channel for retaining particulate matter present in said liquid sample during aspiration of sample into said inlet channel.

6. A method for introducing a well-defined liquid sample into a non-gas segmented liquid carrier stream of a continuous flow analysis system, wherein said method comprises the steps of:

providing an inlet channel having an inlet end and an outlet end; sample means which is selectively connectable to said inlet channel inlet for introducing liquid sample into said inlet channel;

providing a carrier stream channel having an inlet end and an outlet end;

providing an analyzer channel having an inlet end which is connected to the outlet ends of said inlet channel and carrier stream channel to provide a confluence point through which liquids may flow between the inlet channel, carrier stream channel and analyzer channel;

providing first pumping means which is operable at various pumping speeds for pumping a non-gas segmented liquid carrier stream through said carrier stream channel at various selected volumetric flow rates, said flow rates ranging from zero to various predetermined carrier stream flow rates;

providing second pumping means for pumping non-gas segmented liquid through said analyzer channel at a constant predetermined analyzer stream volumetric flow rate wherein said first pumping means is operable at a first selected pumping speed to provide a carrier stream flow rate that is higher than the analyzer stream flow rate in order to flow carrier liquid from said confluence point through said inlet channel towards said inlet channel inlet end and wherein said first pumping means is operable at a second selected pumping speed to provide a carrier stream flow rate that is lower than the analyzer stream flow rate in order to aspirate non-gas segmented liquid sample into said inlet channel when said sample means is connected to the inlet end of said inlet channel, wherein alternating operation of the first pumping means between said first and second pumping speeds provides aspiration of well-defined liquid sample segments into the liquid carrier stream in said analyzer channel;

operating the first pumping means at said first selected pumping speed for a sufficient time to fill said inlet channel with carrier liquid;

connecting said sample means to said inlet channel; operating the first pumping means at said second selected pumping speed for a sufficient time to provide aspiration of liquid sample past said confluence point and into said analyzer channel; and operating the first pumping means at said first selected pumping speed against to thereby provide introduction of a well-defined liquid sample into said liquid carrier stream in said analyzer channel.

7. A method according to claim 6 wherein the second selected pumping speed for said first pumping means is zero.

8. A method according to claim 6 wherein the second pumping speed for said first pumping means is greater than zero to thereby provide dilution of said liquid sample with carrier liquid at said confluence point.

9. A method according to claim 6 for treating liquid samples containing particulate matter wherein a filter is provided in said inlet channel for retaining said particulate matter when said sample is aspirated through said inlet channel, wherein said retained particulate matter is washed from said filter when said first pumping means is operated at said first selected pumping speed.

* * * * *